United States Patent
Thaller

(10) Patent No.: US 11,678,974 B2
(45) Date of Patent: Jun. 20, 2023

(54) METHOD FOR PRODUCING AN INTRAOCULAR LENS, AND PRODUCTION DEVICE

(71) Applicant: Carl Zeiss Meditec AG, Jena (DE)

(72) Inventor: Michael Thaller, Berlin (DE)

(73) Assignee: CARL ZEISS MEDITEC AG, Jena (DE)

(*) Notice: Subject to any disclaimer, the term of this patent is extended or adjusted under 35 U.S.C. 154(b) by 0 days.

(21) Appl. No.: 17/907,326

(22) PCT Filed: Mar. 18, 2021

(86) PCT No.: PCT/EP2021/056896
§ 371 (c)(1),
(2) Date: Sep. 26, 2022

(87) PCT Pub. No.: WO2021/191034
PCT Pub. Date: Sep. 30, 2021

(65) Prior Publication Data
US 2023/0115686 A1  Apr. 13, 2023

(30) Foreign Application Priority Data
Mar. 26, 2020  (DE) ............... 10 2020 108 375.0

(51) Int. Cl.
*A61F 2/16* (2006.01)
*G02C 7/04* (2006.01)
(Continued)

(52) U.S. Cl.
CPC ............ *A61F 2/1613* (2013.01); *A61F 2/16* (2013.01); *A61F 2/1624* (2013.01);
(Continued)

(58) Field of Classification Search
CPC . B29C 35/0805; B29C 61/124; A61F 2/1613; A61F 2/1624
See application file for complete search history.

(56) References Cited

U.S. PATENT DOCUMENTS 10,111,746 B2  10/2018  Wortz et al.
2009/0250828 A1*  10/2009  Rosen ............... B29D 11/00125
425/162

(Continued)

FOREIGN PATENT DOCUMENTS

WO  WO 2019/043529 A1  3/2019
WO  WO 2019/220307 A1  11/2019

OTHER PUBLICATIONS

Golem, "EPFL: New 3D Printing Technology Creates Models in 30 Seconds" ("EPFL: Neue 3D Drucktechnik Erstellt Modelle in 30 Sekunden"), 3 pages, (Feb. 2020). [Retrieved from the Internet Feb. 5, 2021: URL: <https://www.golem.de/news/epfl-neue-3d-drucktechnik-erstellt-modelle-in-30-sekunden-2002-146657.html>].

(Continued)

*Primary Examiner* — William H Matthews
(74) *Attorney, Agent, or Firm* — Alston & Bird LLP

(57) ABSTRACT

The invention relates to a method for producing an intraocular lens, including the steps of providing a container which is transparent to electromagnetic radiation and in which a liquid that is curable by the electromagnetic radiation is arranged; irradiating the liquid with a set of images formed by the electromagnetic radiation, which each depict an intraocular lens, with each of the images of the set being radiated into the liquid at a different angle of incidence with respect to a reference plane that extends through the liquid, as a result of which the liquid is cured and the cured liquid forms the intraocular lens, an actuator, a solar module and/or a sensor being arranged in the liquid and the intraocular lens (Continued)

being formed around the actuator, the solar module and/or the sensor.

9 Claims, 4 Drawing Sheets

(51) Int. Cl.
 *B29C 35/08* (2006.01)
 *B29C 64/124* (2017.01)
(52) U.S. Cl.
 CPC ........ *B29C 35/0805* (2013.01); *B29C 64/124* (2017.08); *G02C 7/04* (2013.01)

(56) References Cited

U.S. PATENT DOCUMENTS

| | | | |
|---|---|---|---|
| 2018/0001581 A1* | 1/2018 | Patel | B29D 11/00961 |
| 2020/0039118 A1 | 2/2020 | Panzer et al. | |
| 2021/0030531 A1* | 2/2021 | Ambati | A61F 2/1637 |

OTHER PUBLICATIONS

"Photopolymer," Wikipedia, 11 pages, (Nov. 12, 2019). [Retrieved from the Internet Feb. 17, 2021: URL: <https://de.wikipedia.org/w/index.php?title=Photopolymer&oldid=193984532#Radikalischer_Mechanismus>].

Office Action of German Application No. 10 2020 108 375.0, dated Feb. 17, 2021.

Written Opinion of the International Searching Authority for PCT/EP2021/056896 (ISA/CN) dated Jul. 2, 2021 (6 pages).

Damien Loterie et al., "High-resolution tomographic volumetric additive manufacturing," Nature Communications, 11(852):1-6, (2020).

Golem, "EPFL: New 3D Printing Technology Creates Models in 30 Seconds" ("EPFL: Neue 3D Drucktechnik Erstellt Modelle in 30 Sekunden"), 3 pages, (Feb. 2020). [Retrieved from the Internet Feb. 5, 2021: URL:< https://www.golem.de/news/epfl-neue-3d-dracktechnik-erstellt-modelle-in-30-sekunden-2002-146657.html >].

"Photopolymer," Wikipedia, 19 pages, (Nov. 17, 2020). [Retrieved from the Internet Feb. 17, 2021: URL: <https://en.wikipedia.org/wiki/Photopolymer#Free_radical_mechanism> (<https://de.wikipedia.org/w/index.php?title=Photopolymer&oldid=193984532#Radikalischer_Mechanismus >)].

PCT International Search Report and Written Opinion of the International Searching Authority, WIPO Application No. PCT/EP2021/056896, dated Jul. 2, 2021.

* cited by examiner

METHOD FOR PRODUCING AN INTRAOCULAR LENS, AND PRODUCTION DEVICE

CROSS-REFERENCE TO RELATED APPLICATIONS

The present application is a national phase entry of International Application No. PCT/EP2021/056896, filed Mar. 18, 2021, which claims priority to German Patent Application No. 10 2020 108 375.0, filed Mar. 26, 2020, which are each incorporated herein by reference in their entirety.

The invention relates to a method for producing an intraocular lens and to a production device for producing the intraocular lens.

Intraocular lenses are conventionally produced by turning. To this end, the material of the intraocular lens is initially produced by polymerization and blanks are subsequently cut from the material. The blanks are then fastened to a turning machine using wax and a computer-controlled robotic arm equipped with a diamond tip cuts the intraocular lens from the blank rotating in the turning machine. Disadvantageously, this is a complicated and hence expensive method. A further disadvantage is that grooves arise on the surface of the intraocular lens during the turning with the diamond tip, with the grooves impairing the optical quality of the intraocular lens.

U.S. Pat. No. 10,111,746 B2 describes a method for producing an intraocular lens.

The object of the invention is therefore to provide a method for producing an intraocular lens and a production device for producing the intraocular lens which can be used to overcome the aforementioned problems.

The method according to the invention for producing an intraocular lens includes the steps of: —providing a container which is transparent to electromagnetic radiation and in which a liquid that is curable by the electromagnetic radiation is arranged; —irradiating the liquid with a set of images formed by the electromagnetic radiation, which each depict an intraocular lens, with each of the images of the set being radiated into the liquid at a different angle of incidence with respect to a reference plane that extends through the liquid, as a result of which the liquid is cured and the cured liquid forms the intraocular lens. This is an advantageously simple method for producing the intraocular lens. Moreover, no grooves arise on the surface of the intraocular lens as a result of the method.

By way of example, the images of the set can be calculated from a three-dimensional data record containing the shape of the intraocular lens. This is a reversed process in relation to a process used in tomographic imaging. By way of example, tomographic imaging is used in computed tomography. By way of example, tomographic imaging can make use of Radon transform.

By way of example, the liquid may contain monomers of a polyacrylate or monomers of a silicone. Moreover, the liquid may contain a photoinitiator, for example camphorquinone.

The intraocular lens is preferably an accommodating intraocular lens. The accommodating intraocular lens is distinguished in that it comprises an optics body which is particularly soft and consequently has the ability to deform, and thus displace its focal spot. A certain minimum stiffness of the material of the intraocular lens is a precondition for the intraocular lens to be produced conventionally by means of turning. However, this minimum stiffness does not allow the intraocular lens to be designed so soft that the accommodating intraocular lens can be created in this way. However, the requirement of minimum stiffness is dispensed with in the method according to the invention, and so the accommodating intraocular lens can be produced. By way of example, the properties of the intraocular lens and, in particular, the stiffness of the intraocular lens can be set by way of a choice of the monomers, a mass ratio of the monomers, a catalyst, the temperature of the liquid and/or reaction times.

The liquid preferably contains oxygen and/or a free-radical scavenger, with the oxygen and/or the free-radical scavenger being dissolved in the liquid. Free-radical scavengers are understood to mean organic or inorganic substances whose chemical reaction with reactive free radicals leads to more stable compounds, with oxygen not considered to be a free-radical scavenger here. Curing of the liquid can be caused by a free-radical polymerization. To this end, the liquid may contain the photoinitiator and the monomers may be configured to undergo a free-radical polymerization. When the liquid is irradiated the photoinitiator decomposes and forms free radicals in the process. The free radicals react with the monomer and the polymer is formed from the monomer by chain growth. The oxygen and/or the free-radical scavenger ensure that the chain growth is terminated or is not even started, and hence curing of the liquid is suppressed. This is illustrated in exemplary fashion by the reaction equations below, where A denotes the monomer and I-I denotes the photoinitiator:

Reaction equation a) represents the decomposition of the initiator. A free radical of the monomer is produced in reaction equation b) and the chain growth is illustrated in reaction equation c). Reaction equation d) illustrates quenching of the free radicals of the decomposing photoinitiator. The liquid can only be cured once the oxygen and/or the free-radical scavenger have been consumed. The oxygen and/or the free-radical scavenger are initially consumed in those regions of the liquid that are irradiated more strongly than the other regions of the liquid. As a result, only the regions of the liquid that should form the intraocular lens are cured.

In a first example, the liquid may have the following composition: 96.97% by weight polydimethylsiloxane with terminal vinyl groups, 3.00% by weight (mercaptopropyl) methylsiloxane-dimethylsiloxane and 0.03% by weight camphorquinone.

In a second example, the liquid may have the following composition: 99.98% by weight aliphatic urethane diacrylic acid and 0.02% by weight camphorquinone.

To saturate the liquid with oxygen, 2 h gaseous oxygen was guided through the liquid in the first example and in the second example. The use of this liquid allowed the production of an intraocular lens so soft that it is suitable as an accommodating intraocular lens.

The images preferably are radiated into the liquid simultaneously. This allows particularly fast production of the intraocular lens.

Alternatively, the images preferably are successively radiated into the liquid while the container is rotated, with the reference plane rotating together with the container. Advantageously, this only requires a single projector for irradiating the liquid with the set of images. The set is particularly preferably radiated in repeatedly and the same images of the repeatedly radiated-in sets are radiated into the liquid under the same angle of incidence.

According to the invention, an actuator, a solar module and/or a sensor is arranged in the liquid and the intraocular lens is formed around the actuator, the solar module and/or the sensor. As a result, further functionalities can be worked into the intraocular lens in addition to the imaging functionality of said intraocular lens.

The method preferably includes the following step: —post-processing the intraocular lens after the latter has been formed. Turning and/or laser ablation are particularly preferably used for said post-processing. As a result, the imaging properties of the intraocular lens can be improved.

The intraocular lens preferably comprises an optics body and at least two haptics, with each of the haptics having a first haptic arm and a second haptic arm which are attached to the optics body at the same site and which include an angle greater than zero in the plane in which the optical axis of the optics body is arranged. These are haptics that cannot be produced in conventional fashion by turning.

The intraocular lens preferably has a cavity. The cavity cannot be produced in conventional fashion by turning.

The production device according to the invention for an intraocular lens comprises a container transparent to electromagnetic radiation and a projection device configured to irradiate an interior of the container with a set of images formed by the electromagnetic radiation and each showing the intraocular lens, and configured to radiate each image of the set into the interior at a different angle of incidence with respect to a reference plane that extends through the interior.

According to the invention, the production device contains the liquid which is arranged in the interior and which is curable by the electromagnetic radiation.

According to the invention, an actuator, a solar module and/or a sensor are arranged in the liquid and the production device is configured to form the intraocular lens around the actuator, the solar module and/or the sensor.

The production device preferably comprises a memory unit in which the images are stored. The memory unit conceivably is part of the projection device in this case.

The projection device preferably comprises, for each image of the set, a respective projector configured to irradiate the interior of the container with the image associated with the projector. Each of the projectors conceivably has a part of the memory unit in this case.

Alternatively, the production device preferably comprises a turning device configured to make the container rotate together with the reference plane, the axis of symmetry of said rotation running through the container, and the projection device preferably comprises a projector configured to successively radiate the images of the set into the container. In this case, it is particularly preferable for the production device to comprise a plurality of said containers and, for each container, a turning device which is configured to make the associated container rotate, the axis of symmetry of said rotation running through the associated container, and for the projection device to be configured to radiate a respective set of images formed by the electromagnetic radiation and each showing an intraocular lens into the interior of every one of the containers, with the projection device being configured to irradiate the containers simultaneously. As a result, a plurality of said intraocular lenses can be produced at the same time. The projection device conceivably comprises a respective projector for each of the containers in this case, with the respective projector being configured to irradiate the associated container. As a result, the plurality of said intraocular lenses can be produced with a different shape. Alternatively, the projection device conceivably comprises a single projector, the beam path of which is split by means of at least one beam splitter into partial beam paths that are each configured to irradiate one of the containers. Advantageously, only one projector is required to simultaneously produce a plurality of said intraocular lenses.

The invention is explained in more detail below with reference to the appended schematic drawings.

Figure 4:
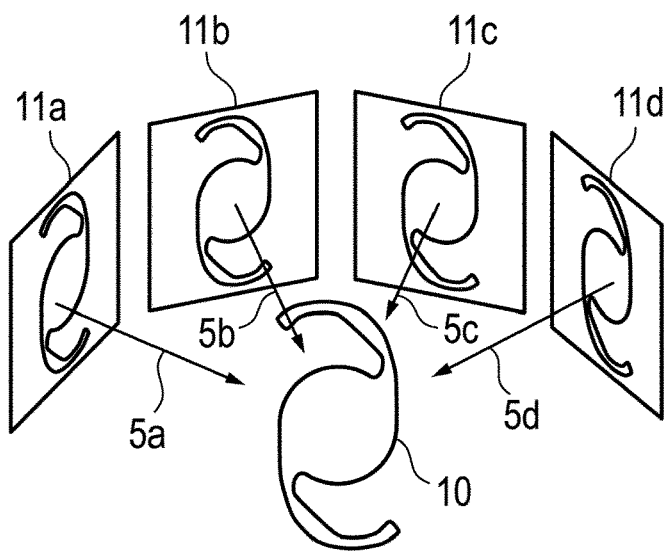

FIG. 4 elucidates the production of an intraocular lens.

Figure 5:
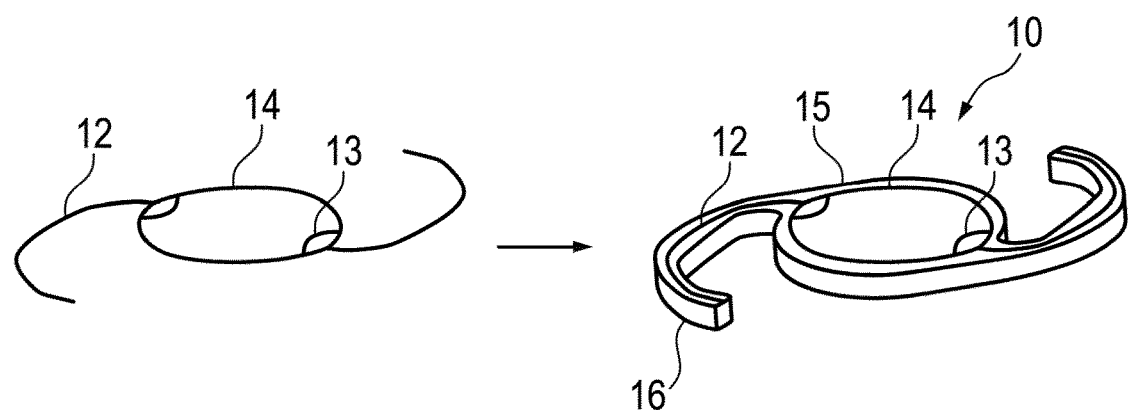

FIG. 5 shows a first embodiment of the intraocular lens.

Figure 6:
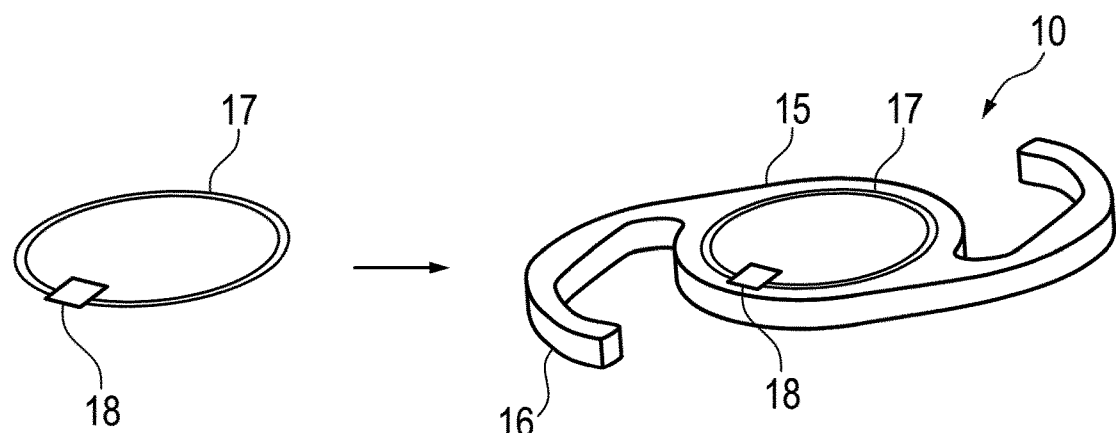

FIG. 6 shows a second embodiment of the intraocular lens.

Figure 7:
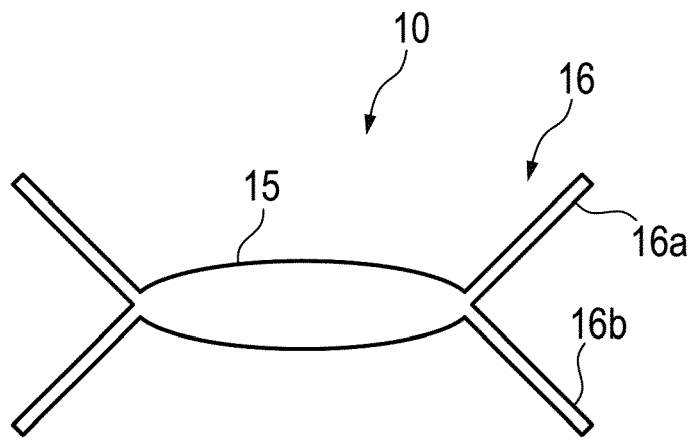

FIG. 7 shows a third embodiment of the intraocular lens.

Figure 8:
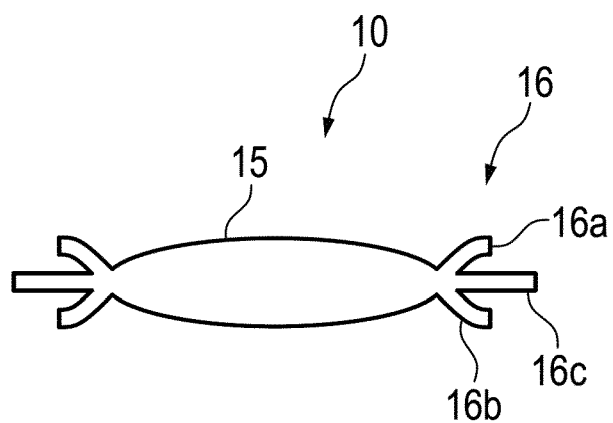

FIG. 8 shows a fourth embodiment of the intraocular lens.

Figure 9:
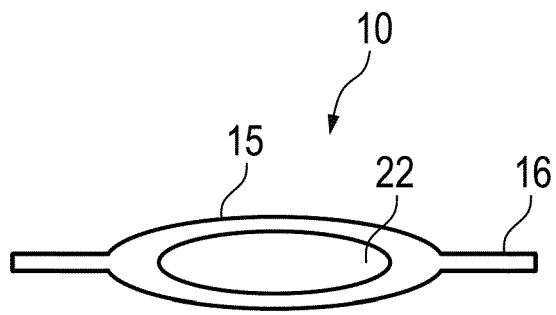

FIG. 9 shows a fifth embodiment of the intraocular lens.

Figure 1:
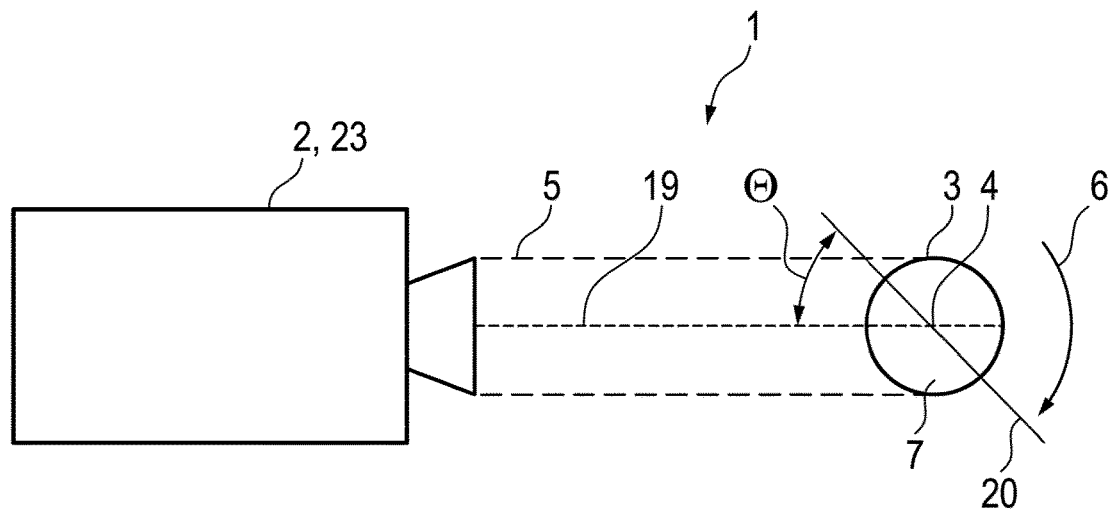
FIG. 1 shows a horizontal section through a first embodiment of a production device according to the invention.
Figure 2:
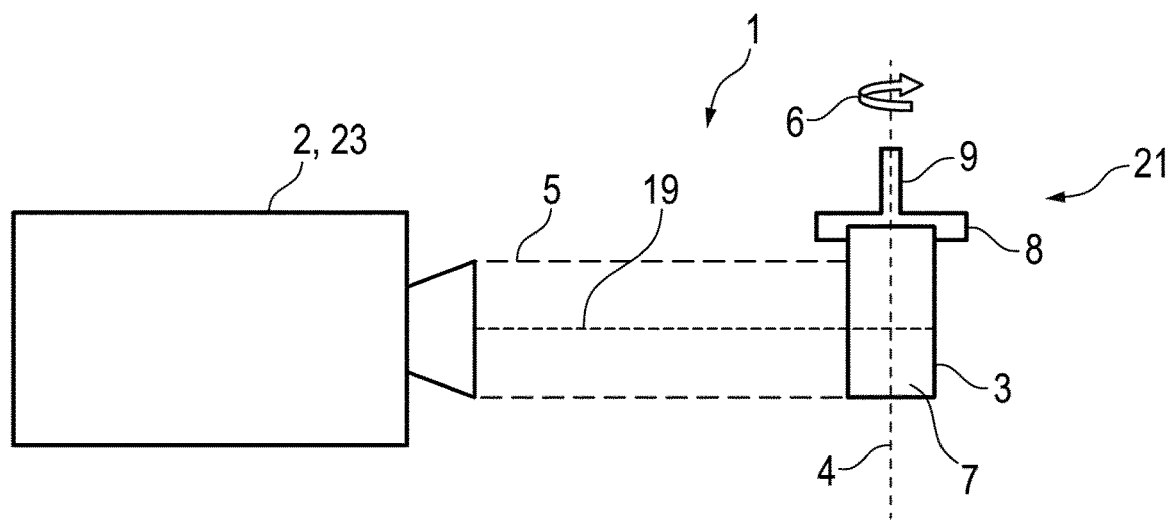
FIG. 2 shows a vertical section through the first embodiment.
Figure 3:
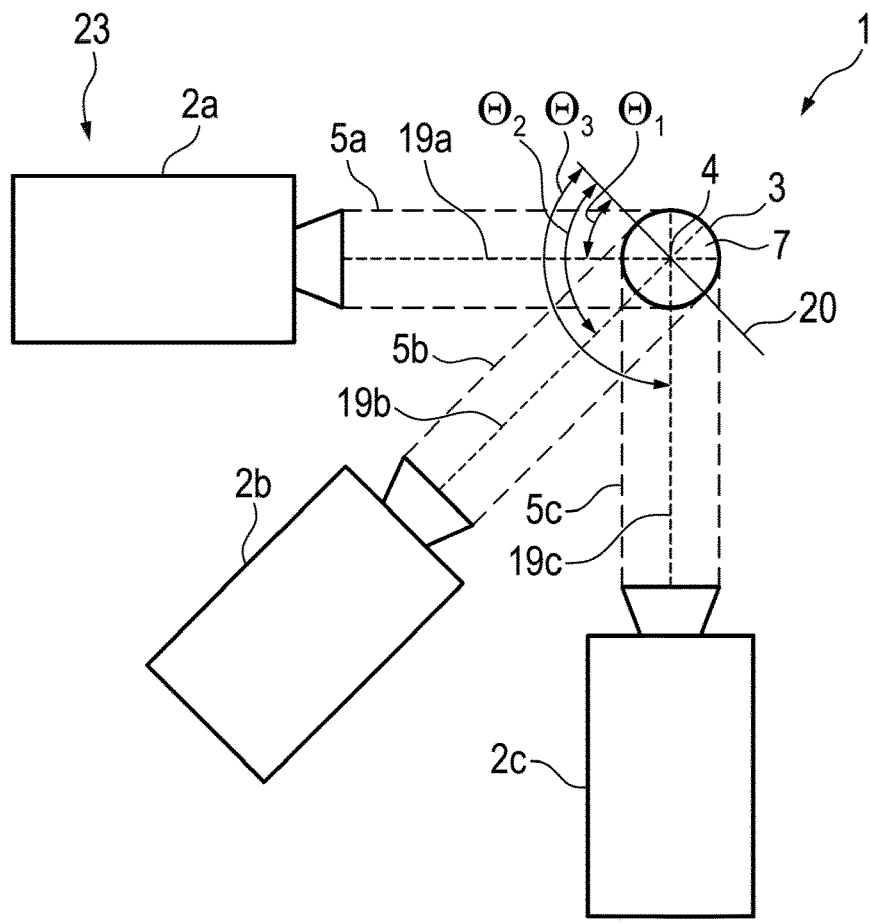
FIG. 3 shows a horizontal section through a second embodiment of the production device according to the invention.

It is evident from FIGS. 1 to 3 that a production device 1, according to the invention, for an intraocular lens 10 comprises a container 3 transparent to electromagnetic radiation and a projection device 23 configured to irradiate an interior of the container 3 with a set of images 11 formed by the electromagnetic radiation and each showing the intraocular lens 10. Moreover, the projection device 23 is configured to radiate each image 11 of the set into the interior at a different angle of incidence θ with respect to a reference plane 20 that extends through the interior. FIGS. 1 and 3 show that the angle of incidence θ may be defined as the angle between an optical axis 19 of a beam path 5 of the electromagnetic radiation incident on the container 3. It is evident from FIGS. 1 to 3 that a wall of the container 3 may have the shape of a cylinder lateral surface, resulting in the interior of the container 3 having the shape of a cylinder. Hence, the interior of the container 3 has an axis of symmetry 4 which is the axis of the cylinder. The axis of symmetry 4 is conceivably located in the reference plane 20, as is also depicted in FIGS. 1 and 3.

The image plane of the beam path 5 can be arranged such that the image plane is located in the interior of the container 3, in particular the image plane can be arranged such that the axis of symmetry 4 is located in the image plane. Moreover, a depth of field extending upstream and downstream of the image plane proceeding from said image plane is conceivably longer than the extent of the optical axis 19 in the interior. Moreover, the beam path 5 conceivably fully illuminates at least a circular cross section of the interior. By way of example, the electromagnetic radiation can be visible light and/or ultraviolet radiation.

The production device 1 may comprise a memory unit in which the images 11 are stored. By way of example, the memory unit may be a part of the projection device 23.

FIGS. 1 to 3 show that the production device 1 may contain a liquid 7 which is arranged in the interior and curable by the electromagnetic radiation. By way of example, the liquid 7 may contain monomers of a polyacrylate or monomers of a silicone. Moreover, the liquid may contain a photoinitiator, for example camphorquinone. The liquid 7 may contain oxygen and/or a free-radical scavenger, with the oxygen and/or the free-radical scavenger being dissolved in the liquid. Free-radical scavengers are understood to mean organic or inorganic substances whose chemical reaction with reactive free radicals leads to more stable compounds, with oxygen not considered to be a free-radical scavenger here. Curing of the liquid 7 can be caused by a free-radical polymerization. To this end, the liquid 7 may contain the photoinitiator and the monomers may be configured to undergo a free-radical polymerization.

A first embodiment of the production device 1 according to FIGS. 1 and 2 comprises a turning device 21 configured to make the container 3 rotate together with the reference plane 20, the axis of symmetry 4 of said rotation running through the container 3, and the projection device 23 comprises a projector 2 configured to successively radiate the images 11 of the set into the container 3. In this case, the reference plane 20 and the container 3 rotate at the same angular speed. The axis of symmetry 4 of the rotation may coincide with the axis of symmetry of the container 3. An exemplary direction of rotation 6 is plotted in FIGS. 1 and 2. The rotation device 21 may comprise a holder 8 which engages around the container 3 from above. Moreover, the turning device 21 may have a rotary shaft 9 which is securely attached to the holder 8 and configured to be put into rotation by a motor of the turning device when said turning device 21 is in operation.

In the case of the first embodiment, the production device 1 conceivably comprises a plurality of said containers 3 and, for each container, a turning device 21 which is configured to make the associated container 3 rotate, the axis of symmetry 4 of said rotation running through the associated container 3, and the projection device 23 is conceivably configured to radiate a respective set of images 11 formed by the electromagnetic radiation and each showing an intraocular lens 10 into the interior of every one of the containers 3, with the projection device 23 being configured to irradiate the containers 3 simultaneously. The projection device 23 conceivably comprises a respective projector 2 for each of the containers 3 in this case, with the respective projector being configured to irradiate the associated container 3. In this case, the projectors 2 are conceivably configured to in each case radiate a different set of said images 11 into the respective interior. Alternatively, the projection device 23 conceivably comprises a single projector 2, the beam path 5 of which is split by means of at least one beam splitter into partial beam paths that are each configured to irradiate one of the containers 3.

In a second embodiment of the production device 1 according to FIG. 3, the projection device 23 comprises, for each image 11 of the set, a respective projector 2a, 2b, 2c configured to irradiate the interior of the container 3 with the image 11 associated with the projector 2. As is evident from FIG. 3, a respective beam path 5a, 5b, 5c with a respective optical axis 19a, 19b, 19c belongs to each of the projectors 2a, 2b, 2c, with each of the optical axes 19a, 19b, 19c in each case including a different angle of incidence 81, 82, 83 with the reference plane 20.

FIG. 4 elucidates an exemplary set of said images 11a to 11d with which the intraocular lens 10 is producible, it clearly being evident that each of the images 11a to 11d is formed by a different beam path 5a to 5d and each beam path 5a to 5d is radiated in at a different angle of incidence θ with respect to the reference plane 20. By way of example, the images 11 of the set can be calculated from a three-dimensional data record containing the shape of the intraocular lens 10. This is a reversed process in relation to a process used in tomographic imaging. By way of example, tomographic imaging is used in computed tomography. By way of example, tomographic imaging can make use of Radon transform.

FIG. 5 shows a first embodiment of the intraocular lens 10, which was produced by virtue of an actuator 13 being arranged in the liquid 7 and the intraocular lens 10 being formed around the actuator 13. A haptic 16 of the intraocular lens 10 can be bent following the insertion of said intraocular lens 10 into a capsular bag of an eye in a first embodiment of the intraocular lens 10. This enables retrospective modification of the position of the intraocular lens 10, for example in order to centre or rotate said intraocular lens 10. To this end, the intraocular lens 10 comprises a ring 14 and a bendable arm 12, securely attached to the ring 14, for each of the haptics 16, and one of the actuators 13 for each of the haptics 16. Each actuator 13 is configured to alter the angle between the bendable arm 12 and the ring 14. The arrangement made of the ring 13, the bendable arms 12 and the actuators 13, as is to be inserted into the liquid 7, is depicted to the left in FIG. 5. The completed intraocular lens 10 is depicted to the right in FIG. 5, with each of the haptics 16 having been formed around one of the movable arms 12 and an optics body 15 of the intraocular lens 10 having been formed around the ring 14. Moreover, in order to supply the actuators 13 with power, the intraocular lens 10 may comprise a solar module, which was arranged in the liquid 7 and around which the intraocular lens 10 was formed and which is configured to convert light into electrical current.

FIG. 6 shows a second embodiment of the intraocular lens 10, which was produced by virtue of a sensor 18 being arranged in the liquid 7 and the intraocular lens 10 being formed around the sensor 18. Moreover, the intraocular lens 10 may comprise a circuit 17 and/or a solar module, configured to convert light into current and supply the sensor 18 and/or the circuit with current. The arrangement made of the sensor 18 and optionally the circuit 17 and/or the solar module, as is to be inserted into the liquid 7, is depicted to the left in FIG. 6. The completed intraocular lens 10 is depicted to the right in FIG. 6.

FIG. 7 depicts a third embodiment of the intraocular lens 10 and FIG. 8 depicts a fourth embodiment of the intraocular lens 10, in which the intraocular lens 10 comprises an optics body 15 and at least two haptics 16, with each of the haptics 16 having a first haptic arm 16a and a second haptic arm 16b which are attached to the optics body 15 at the same site and which include an angle greater than zero in a plane in which the optical axis of the optics body 15 is arranged. It is evident from FIG. 7 that each of the haptics 16 according to the third embodiment may consist of the first haptic arm 16a and the second haptic arm 16b. It is evident from FIG. 8 that, according to the fourth embodiment, each of the haptics 16 may have a third haptic arm 16c, which is attached to the optics body 15 at the same site as the first haptic arm 16a and the second haptic arm 16b and which is arranged between the first haptic arm 16a and the second haptic arm 16b.

FIG. 9 depicts a fifth embodiment of the intraocular lens 10, which has a cavity 22. By way of example, the cavity 22 can be arranged in an optics body 15 of the intraocular lens 10. Alternatively or in addition, the cavity 22 is conceivably arranged in a haptic 16 of the intraocular lens.

LIST OF REFERENCE SIGNS

1 Production device
2 Projector

2a Projector
2b Projector
2c Projector
3 Container
4 Axis of symmetry
5 Beam path
5a Beam path
5b Beam path
5c Beam path
5d Beam path
6 Direction of rotation
7 Liquid
8 Holder
9 Axis of rotation
10 Intraocular lens
11 Image
11a Image
11b Image
11c Image
11d Image
12 Bendable arm
13 Actuator
14 Ring
15 Optics body
16 Haptic
16a First haptic arm
16b Second haptic arm
16c Third haptic arm
17 Circuit
18 Sensor
19 Optical axis
19a Optical axis
19b Optical axis
19c Optical axis
20 Reference plane
21 Turning device
22 Cavity
23 Projection device
$\theta$ Angle of incidence
$\theta_1$ Angle of incidence
$\theta_2$ Angle of incidence
$\theta_3$ Angle of incidence

The invention claimed is:

1. Method for producing an intraocular lens, including the steps of:
   providing a container which is transparent to electromagnetic radiation and in which a liquid that is curable by the electromagnetic radiation is arranged;
   irradiating the liquid with a set of images formed by the electromagnetic radiation, which each depict an intraocular lens, with each of the images of the set being radiated into the liquid at a different angle of incidence with respect to a reference plane that extends through the liquid, as a result of which the liquid is cured and the cured liquid forms the intraocular lens, an actuator, a solar module and/or a sensor being arranged in the liquid and the intraocular lens being formed around the actuator, the solar module and/or the sensor.

2. Method according to claim 1, wherein the intraocular lens is an accommodating intraocular lens.

3. Method according to claim 1, wherein the liquid contains oxygen and/or a free-radical scavenger, with the oxygen and/or the free-radical scavenger being dissolved in the liquid.

4. Method according to claim 1, wherein the images are radiated into the liquid simultaneously.

5. Method according to claim 1, wherein the images are successively radiated into the liquid while the container is rotated, with the reference plane rotating together with the container.

6. Method according to claim 1, including the step of:
   post-processing the intraocular lens after the latter has been formed, turning and/or laser ablation in particular being used for said post-processing.

7. Production device for an intraocular lens, comprising a container transparent to electromagnetic radiation and a projection device configured to irradiate an interior of the container with a set of images formed by the electromagnetic radiation and each showing the intraocular lens, and configured to radiate each image of the set into the interior at a different angle of incidence with respect to a reference plane that extends through the interior, the production device containing a liquid which is arranged in the interior and which is curable by the electromagnetic radiation, with an actuator, a solar module and/or a sensor being arranged in the liquid and the production device being configured to form the intraocular lens around the actuator, the solar module and/or the sensor.

8. Production device according to claim 7, wherein the production device comprises a turning device configured to make the container rotate together with the reference plane, the axis of symmetry of said rotation running through the container, and the projection device comprises a projector configured to successively radiate the images of the set into the container.

9. Production device according to claim 8, wherein the production device comprises a plurality of said containers and, for each container, a turning device which is configured to make the associated container rotate, the axis of symmetry of said rotation running through the associated container, and the projection device is configured to radiate a respective set of images formed by the electromagnetic radiation and each showing an intraocular lens into the interior of every one of the containers, with the projection device being configured to irradiate the containers simultaneously.

* * * * *